United States Patent
Fleissner

(10) Patent No.: US 6,254,821 B1
(45) Date of Patent: Jul. 3, 2001

(54) DEVICE FOR PRODUCING A VOLUMINOUS BONDED FLEECE, DEVICE IMPLEMENTING THE METHOD, AND BONDED FLEECE ACCORDING TO THIS METHOD

(75) Inventor: Gerold Fleissner, Zug (CH)

(73) Assignee: Fleissner GmbH Co., Maschinenfabrik, Egelsbach (DE)

( * ) Notice: Subject to any disclaimer, the term of this patent is extended or adjusted under 35 U.S.C. 154(b) by 0 days.

(21) Appl. No.: 09/129,602

(22) Filed: Aug. 5, 1998

(30) Foreign Application Priority Data

Aug. 6, 1997 (DE) .............................. 197 33 933
Aug. 16, 1997 (DE) .............................. 197 35 667

(51) Int. Cl.⁷ ...................................... B27N 3/04
(52) U.S. Cl. ..................... 264/518; 264/113; 156/167
(58) Field of Search ................... 264/122, 518, 264/113, 112; 156/167

(56) References Cited

U.S. PATENT DOCUMENTS

| | | | | |
|---|---|---|---|---|
| 4,118,531 | * | 10/1978 | Hauser | 428/224 |
| 4,568,581 | * | 2/1986 | Peoples, Jr. | 428/35 |
| 4,783,231 | * | 11/1988 | Raley | 156/167 |
| 5,108,820 | * | 4/1992 | Kaneko et al. | 428/198 |
| 5,396,689 | * | 3/1995 | Vuillaume | 28/103 |
| 5,701,643 | * | 12/1997 | Fleissner | 28/105 |

FOREIGN PATENT DOCUMENTS

0171806 * 2/1986 (EP) .
0171807 * 2/1986 (EP) .

* cited by examiner

*Primary Examiner*—Mary Lynn Theisen
(74) *Attorney, Agent, or Firm*—Antonelli, Terry, Stout & Kraus, LLP

(57) ABSTRACT

Bulked and liquid-permeable fleeces are used in the hygienic products industry for diapers and bandages. These fleeces have the purpose of rapidly absorbing fluid secreted from the body, storing it, and slowly giving it up to the absorber located beneath, uniformly over the entire surface of the absorber. As a result of the idea according to the invention, a fleece is formed from shrunk and/or crimped fibers together with non-shrinking man-made fibers, and the fleece is then compacted by a hydrodynamic compacting method without using binders, after which the fleece is dried and the shrinking ability present in the shrinking fibers and/or the crimping ability present in the crimping fibers in latent form are triggered immediately and/or subsequently by the action of temperature. This fleece can be manufactured economically and meets all of the requirements imposed upon it.

13 Claims, 1 Drawing Sheet

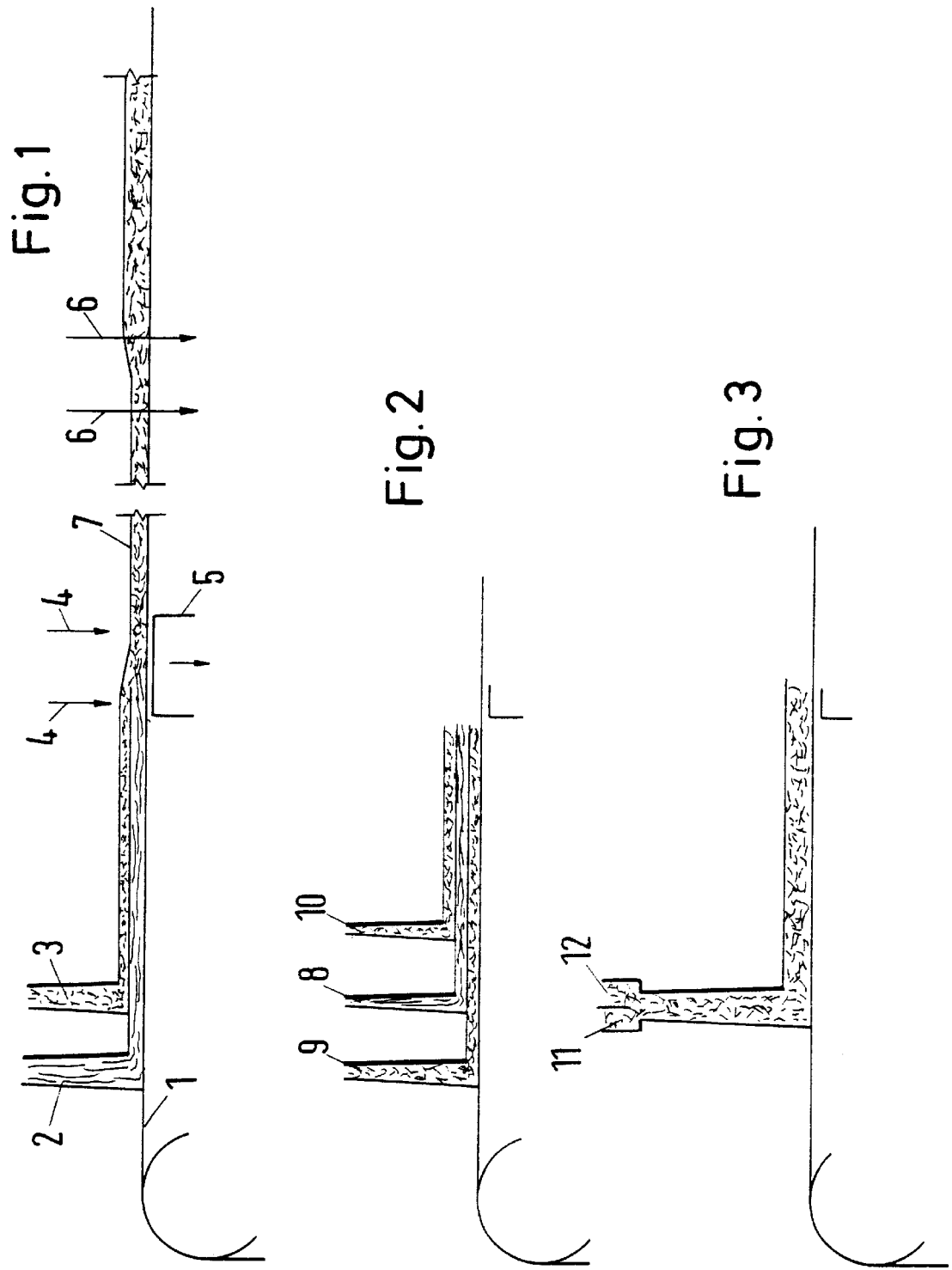

DEVICE FOR PRODUCING A VOLUMINOUS BONDED FLEECE, DEVICE IMPLEMENTING THE METHOD, AND BONDED FLEECE ACCORDING TO THIS METHOD

It is known from U.S. Pat. No. 4,118,531 to use crimped fibers to produce a bulked fleece. For this purpose, the crimped fibers are laid down in a stream together with other smooth fibers. However, since such a fleece must be compacted, the fleece must be mechanically compressed, causing it to lose a significant part of its volume once again.

It is known from U.S. Pat. No. 5,108,820 to use bicomponent fibers to make a bulked fleece, with the components of these fibers shrinking differently when heated, and with the fibers crimping three-dimensionally. These fibers or other single-component fibers that crimp under the influence of heat are laid down together with other fibers to form a fleece which must however be compressed by pressure for compaction, so that it loses volume.

Another use of bicomponent fibers is described in EP-A-0 171 806 or 0 171 807. In that case, the bicomponent fibers laid down with other fibers to produce a first compaction is subjected to thin streams of water and then the fleece product is heated to the sticking or melting temperature of one component of the bicomponent fiber so that this molten component connects permanently to the other fibers, producing a second compaction. In this way, a fleece product can be produced that is solid but not bulked.

A bonded fleece that is both bulked and permeable to liquid is used in the hygienic products industry. In diapers or other hygienic products, a fluid buffer must initially be provided that ensures drainage of the excreted body fluid into the absorber located adjacent thereto in the transverse and also, and especially, in the lengthwise direction. The liquid buffer must quickly absorb the liquid flowing out and then pass it on slowly to the adjacent absorber over its entire surface.

The goal of the invention is to develop an economical method by which a bulked and sufficiently compacted fleece can be produced without the aid of chemical binders or gluing, said fleece having sufficient room for rapid absorption of the excreted liquid and distributing the liquid uniformly over the surface of the fleece for drainage. As a result, the adjacent absorber has the ability to absorb the liquid slowly and completely from this volume.

To achieve this stated goal, the invention provides that a fleece is formed from shrunk and/or crimped fibers together with non-shrinking manmade fibers, the fleece is then compacted using a hydrodynamic compaction method without using binders, and the fleece is then dried, and then at this point and/or subsequently, the shrinkage present in the shrunk fibers and/or the crimping ability present in the crimped fibers in latent form are triggered by the action of heat. If the shrinkage or crimping is to be triggered chemically, this processing step likewise comes under the subject of the invention. A fleece of this kind is bulked because of the way it is made. The volume increases only slightly as a result of water needling, but resumes its volume as a result of the shrinkage or crimping of the fibers, in such fashion that the new fleece is optimally correct at its point of application for the properties desired of hygienic products.

The fleece can be made of staple fibers and/or endless fibers. The shrunk and/or crimped fibers can be mixed in advance with the fibers that do not change, or the layer of fibers that change under the influence of heat can be applied on one or both sides. Advantageously, bicomponent fibers of the "side by side" type are used (U.S. Pat. No. 5,108,820), with a fiber component deposited laterally on the fibers undergoing a change in length under the influence of temperature. As a result, the fiber is deformed three-dimensionally overall, so that fleece becomes compacted and bulkier. The same applies to the pure shrunk fibers (monopolymers) which according to the invention is [sic] water-needled with non-shrinking fibers so that after the shrinking process, the entire fiber fleece changes so that it has more volume. The pile weight can be between 3 and 60 g/m² with a fiber titer of 1.3–6.7 dtex.

A device for working a method of the species according to the invention is shown only schematically in the drawing.

FIG. 1 is a schematic view of a system for producing a compacted bonded fleece composed of two fiber layers, with the shrinking or crimping fiber layer being located only unilaterally in the fleece;

FIG. 2 shows the same arrangement as in FIG. 1 but for a fleece with three layers, with the shrinking or crimping fiber layers being located on the top and bottom; and FIG. 3 shows the same arrangement as in FIG. 1 but for a fleece consisting of only one layer of fibers, said layer being composed of fibers of the stated type mixed with another before the fleece is laid down.

The system consists of a plurality of machines arranged one after the other that operate continuously to deliver the desired bulked fleece at the end of the processing method. The endless belt marked 1 initially serves only to form the fleece and then to transport it into and through the individual processing machines. According to FIG. 1, the fleece consists of two layers, namely endless fibers from shaft 2 and staple fibers from shaft 3. The staple fibers are supposed to be the shrink fibers in this case. They are therefore essentially arranged only unilaterally in the fleece structure.

The fleece-laying unit is adjoined by a hydrodynamic needling device marked 4 in FIG. 1. It generally consists of a plurality of nozzle beams that extend transversely across the working width of the fleece and of a plurality of fine jets of water at high pressure that spray through the fleece. As a result, the individual fibers of the fleece are mixed with one another and hooked, compacting the fleece without the aid of chemical binders. The water is drawn off again below endless belt 1 as indicated by suction box 5.

As a result of the hydraulic compaction process, the fleece laid down previously has its volume reduced, but this is followed by the drying process and the process of shrinking and/or crimping the shrink and/or crimp fibers. The fleece is to be dried by flow through the goods, as indicated by the two arrows 6 shown in the drawing. Endless belt 1 can be followed by a shaft dryer for this purpose but it is more efficient to place the compacted fleece 7 alone in a separately organized dryer such a screen drum dryer for example. The necessary drying then takes place in this heat treatment assembly, possibly followed immediately by shrinking and/or crimping of the existing shrink and/or crimp fibers as well as the bicomponent fibers of a special type. The shrinking and/or crimping processes however can also take place in a special adjoining shrinking and/or crimping oven.

The system in FIGS. 2 and 3 is the same as in FIG. 1 except that the fleece to be processed consists of three layers in FIG. 2 and of only one layer in FIG. 3. The fleece according to FIG. 2 consists of a central endless fiber layer 8 on both of whose sides staple fibers 9, 10 made of shrink fibers and/or crimp or bicomponent fibers of the special type are located. In the hydrodynamic needling station, layers 8 to 10 are mixed with one another. In the type of fleece according to FIG. 3, the various fibers 11, 12 have already been mixed with one another during the laying down of the fleece. Depending on the application, one or another type of fleece may be advantageous.

What is claimed is:

1. Method for producing a fleece from artificial fibers, characterized in that a fleece made of shrink and/or crimp fibers is formed together with non-shrinking man-made fibers, the latter is compacted by a hydrodynamic compacting method without using binders, and the fleece is then dried, and immediately and/or subsequently the shrinking ability present in the shrink fibers and/or crimping ability present in the crimp fibers latent form are triggered under the influence of temperature.

2. Method according to claim 1, characterized in that the fleece is formed from endless fibers.

3. Method according to claim 1 or 2, characterized in that the fleece is formed from staple fibers.

4. Method according to claim 1 or 2, characterized in that the fleece is produced at least partially from fibers that crimp under the influence of temperature.

5. Method according to claim 1 or 2, characterized in that during the formation of a fleece, the shrink and/or crimp fibers are laid down unilaterally on a fleece made of non-shrinking fibers and the two fleece layers are also bonded to one another by water needling.

6. Method according to claim 1 or 2, characterized in that the shrink and/or crimp fibers are laid down on both sides of a fleece made of non-shrinking fibers and these three fleece layers are bonded to one another by water-needling.

7. Method according to claim 3, characterized in that the fleece is produced at least partially from fibers that crimp under the influence of temperature.

8. Method according to claim 5, characterized in that during the formation of a fleece, the shrink and/or crimp fibers are laid down unilaterally on a fleece made of non-shrinking fibers and the two fleece layers are also bonded to one another by water needling.

9. Method according to claim 3, characterized in that the shrink and/or crimp fibers are laid down on both sides of a fleece made of non-shrinking fibers and these three fleece layers are bonded to one another by water-needling.

10. Method according to claim 4, characterized in that the shrink and/or crimp fibers are laid down on both sides of a fleece made of non-shrinking fibers and these three fleece layers are bonded to one another by water-needling.

11. Method according to claim 5, characterized in that the shrink and/or crimp fibers are laid down on both sides of a fleece made of non-shrinking fibers and these three fleece layers are bonded to one another by water-needling.

12. Method according to claim 1, characterized in that the artificial fibers are selected from the group consisting of PES and polyolefin fibers.

13. Method according to claim 4, characterized in that the fibers that crimp under the influence of temperature are side-by-side bicomponent fibers.

* * * * *